United States Patent [19]
Johnson et al.

[11] Patent Number: 5,664,109
[45] Date of Patent: Sep. 2, 1997

[54] METHOD FOR EXTRACTING PRE-DEFINED DATA ITEMS FROM MEDICAL SERVICE RECORDS GENERATED BY HEALTH CARE PROVIDERS

[75] Inventors: Gary Duane Johnson, Lewisville; Kelly Scott Campbell, Richardson, both of Tex.

[73] Assignee: E-Systems, Inc., Dallas, Tex.

[21] Appl. No.: 483,469

[22] Filed: Jun. 7, 1995

[51] Int. Cl.$^6$ .............................. G06F 17/30; G06F 13/36
[52] U.S. Cl. ........................ 705/2; 395/54; 395/791; 395/610; 395/602; 395/924; 705/3; 705/4
[58] Field of Search .................... 395/603, 202, 395/203, 204, 924, 610, 602, 791, 54; 364/DIG. 1

[56] References Cited

U.S. PATENT DOCUMENTS

| | | | |
|---|---|---|---|
| 4,858,121 | 8/1989 | Barber et al. | 364/406 |
| 4,916,611 | 4/1990 | Doyle, Jr. et al. | 364/401 |
| 4,965,763 | 10/1990 | Zamora | 364/900 |
| 5,159,552 | 10/1992 | Van Gasteren et al. | 364/419 |
| 5,159,667 | 10/1992 | Borrey et al. | 395/148 |
| 5,164,899 | 11/1992 | Sobotka et al. | 364/419 |
| 5,182,705 | 1/1993 | Barr et al. | 364/401 |
| 5,225,976 | 7/1993 | Tawil | 364/401 |
| 5,241,671 | 8/1993 | Reed et al. | 395/600 |
| 5,267,155 | 11/1993 | Bechanan et al. | 364/419.14 |
| 5,297,249 | 3/1994 | Bernstein et al. | 395/156 |
| 5,301,105 | 4/1994 | Cummings, Jr. | 364/401 |
| 5,327,341 | 7/1994 | Whalen et al. | 364/413.01 |
| 5,404,295 | 4/1995 | Katz et al. | 364/419.19 |
| 5,414,644 | 5/1995 | Seaman et al. | 364/551.01 |
| 5,471,382 | 11/1995 | Tallman et al. | 364/406 |
| 5,519,607 | 5/1996 | Tawil | 364/401 |
| 5,528,492 | 6/1996 | Fukushima | 364/419.19 |
| 5,542,420 | 8/1996 | Goldman et al. | 128/630 |
| 5,581,479 | 12/1996 | McLaughlin et al. | 364/514 |

OTHER PUBLICATIONS

"Why Fastrack Medstat is King of the On-Line Health Claims Analysis Roads" Automated Medical Payment News, Vol. 1, No. 9, pp. 112–115; Dec. 6, 1992.

Susan Demorsky— "Automation of Medical Records Can Boost Cash Flow," Healthcare Financial Management, V44, N10, pp.20–27; Oct. 1990.

*Primary Examiner*—Thomas G. Black
*Assistant Examiner*—Jean R. Homere
*Attorney, Agent, or Firm*—Harold E. Meier

[57] ABSTRACT

A central medical record repository for a managed health care organization accepts and stores medical record documents in any format from medical service providers. The repository then identifies the document using information automatically extracted from the document and stores the extracted data in a document database. The repository links the document to a patient by extracting from the document demographic data identifying the patient and matching it to data stored in a patient database. Data is extracted automatically from medical records containing "unstructured" or free-form text by identifying conventional organization components in the text and is organized by executing rules that extract data with the aid of such information. Documents for a patient are retrieved by identifying the patient using demographic data.

11 Claims, 7 Drawing Sheets

FIG. 9

```
CREATION:
MetaTag version 1.3
080695.1340.12
HEADER
start xxx, end yyy
TITLE.
start nnn, end zzz
SUBJECT.patient.
start aaa, end bbb
BODY SECTION 1.symptoms.
start hhh, end ttt
        etc.
```

900

METHOD FOR EXTRACTING PRE-DEFINED DATA ITEMS FROM MEDICAL SERVICE RECORDS GENERATED BY HEALTH CARE PROVIDERS

FIELD OF THE INVENTION

The invention relates to the field of data processing systems and more particularly to automated document identification and indexing.

BACKGROUND OF THE INVENTION

Medical or health care services are traditionally rendered by numerous providers who operate independently of one another. Providers may include, for example, hospitals, clinics, doctors, therapists and diagnostic laboratories. A single patient may obtain the services of a number of these providers when being treated for a particular illness or injury. Over the course of a lifetime, a patient may receive the services of a large number of providers. Each medical service provider typically maintains medical records for services the provider renders for a patient, but rarely if ever has medical records generated by other providers. Such documents may include, for example, new patient information or admission records, doctors' notes, and lab and test results. Each provider will identify a patient with a medical record number (MRN) of its own choosing to track medical records the provider generates in connection with the patient.

Due to increasing costs, providers are being grouped by insurance companies, hospitals and other organizations and are setting up formal networks of medical service providers. Medical service providers are joining these networks or organizations in order to compete for patients. The networks typically negotiate fixed prices for medical services and supplies. Furthermore, the networks manage the services dispensed by developing sets of standard practice rules and managing referrals to specialists to insure that specialty services are medically necessary.

In order to make health care management more efficient, improve the quality of health care delivered and eliminate inefficiencies in the delivery of the services, there is a desire to collect all of a patient's medical records into a central location for access by health care managers and providers. A central database of medical information about its patients enables a network or organization to determine and set practices that help to reduce costs. It also fosters sharing of information between health care providers about specific patients that will tend to improve the quality of health care delivered to the patients and reduce duplication of services.

There are several impediments to centralizing and sharing medical records. First, there is the cost in equipment, software and personnel required to collect and process medical records at a central location, and in responding to requests for medical records. Medical records present special problems due to their diversity in form and content. In order to efficiently process the medical records for subsequent access, standardized procedures, forms and reporting must be developed and adopted by the entire network of providers. Second, there is the cost and reluctance of the independent medical service providers in conforming to standardized practices typically required for a central record keeping system. Since most medical service providers have preexisting or "native" record keeping systems, these would have to be converted and a unique medical record number or patient identifier assigned to each patient. Standardizing medical record keeping, including unique patient identifiers within a network, may, however, be complicated by the loose and fluid nature of such networks. A provider may be member of several networks. Medical service providers are constantly added and dropped from networks and health care organizations, or parts thereof, may merge or split apart. Thus, a provider would not only have to keep multiple identifiers, the provider would also be further burdened with additional and changing standards. Providers are unlikely to have the resources and expertise to accommodate the requirements of changing or multiple networks.

SUMMARY OF THE INVENTION

According to the present invention, a centralized record keeping system receives record documents from one of a plurality of independent service providers. The system automatically links the record to a person who is the subject of the record by automatically extracting from the record demographic data on the subject and matching it to demographic data on the subject maintained in a database. Unique subject identifiers are not preassigned by the central record keeping system or used for linking. The records are stored in a repository and a list of linked records is maintained for each person. All records for a particular subject are then available for retrieval by querying the database of demographic data.

In the context of a managed health care network, all providers who subscribe to or are members of a health care organization or network need not adopt standard patient identifiers or medical formats, hardware and software. The providers are able to continue to use their preexisting information systems, including medical record numbers or patient identifiers. Yet medical records are easily shared with other providers within the organization. Thus, the invention enables the collection and analysis of patient information without imposing significant extra cost and overhead on the providers.

In one embodiment of the invention, medical service providers send or transmit documents containing medical record information of a patient to a central data processing system. The system stores the document and automatically links it to a master record maintained by the system for each patient. The linking to a patient is based on "demographic" data contained in the document. The patient's master record contains basic demographic data on the patient, including a list of medical record numbers and other references assigned by the medical providers to the patient that are known to the central system. In order to associate or link a document to a patient, the system attempts first to automatically extract the medical record number, as well as patient demographic data, from the record. The extracted patient demographics are matched to demographic information contained in the master patient records. After an association is made, the document record is linked to the patient record for subsequent access by other authorized providers and subscribers to the system through the patient demographic database. The system maintains only one master record per patient. When a match cannot be made, a new patient record may be created and subsequently merged if it is later determined that two records exist for the same patient. Fuzzy links may be established between a medical document and a master patient record when the degree of confidence in the match is not high. These fuzzy links then may be subsequently reviewed for resolution by human judgment or additional matching processes.

Globally unique medical record numbers or patient identifiers are thus not necessary. Different providers, or providers with heterogeneous systems, are able to subscribe to an integrated health care network without the cost and difficulty of adopting standardized medical record numbers, patient identifiers and rigid document formats. The providers may continue to use their own medical record numbers or other patient identifiers and to submit documents, reports and data in any desired format and through any medium desired. Furthermore, matching demographic data tends to provide a high degree of confidence that a medical record has been properly associated to a proper patient.

A subscriber has the option of being notified of receipt of medical records for one of its patients that is submitted by another provider. By notifying providers caring for the same patient of new medical records for the patient, duplicate procedures may be eliminated and overall medical care monitored by one or more providers, thus reducing costs and improving the quality of medical care for a patient.

The patient demographic database is automatically populated using information extracted from certain documents such as an admission or registration document. If no match between a document and a patient can be made, a new patient demographic record is set up and populated with information from the document. After a match is made, demographic data stored in the master patient record is compared with information contained in the new document and the master patient record updated if necessary.

In order to automatically catalog documents, identifying information is also extracted and stored in a document identifier database for cataloging the documents and assisting subsequent retrieval of particular documents. These identifiers are automatically extracted when the documents are received. These identifiers include, for example, the name of the source organization of the document and the type of document.

Document identifiers and patient demographic information in medical records come in one of two basic forms. In one form, these data items are logically arranged into data fields having a predefined format. Data from these records are readily extracted by automated methods using templates and keyword location techniques. However, many types of medical records, are not organized into any particular form or format. Furthermore, data items that are to be extracted may be located in text which has not been organized or structured into fields. In accordance with another aspect of the invention, document identifiers and patient demographic data are automatically extracted from unfielded, free-form text of a document by first identifying conventional structural components into which the free-form text is spatially organized in the document, for example headers, footers, title and body sections. Data is then extracted by executing a series of rules using, as necessary, knowledge of the identified structure. For example, when extracting the name of an originator of a document, first the document header and then its title is searched for a name string matching stored name strings for providers. Thus, a medical record need not be submitted in a standardized or structured format for automated data extraction.

In accordance with still another aspect of the invention, conventional structural elements of free-form or unfielded text are tagged with a medically relevant term to facilitate subsequent location and retrieval of only a portion of text of a document by automatically identifying the sections as being of a particular type.

The foregoing summary is intended only as a summary of the various aspects of the disclosed embodiment of the invention and should not be construed as limiting the scope of the invention as set forth in the appended claims. Additional aspects and advantages of the invention will be apparent from the following description of a preferred embodiment illustrated by the accompanying drawings.

BRIEF DESCRIPTION OF THE DRAWINGS

In the appended drawings,

FIG. 9 illustrates a representative file in which tags corresponding to structural elements of the document of FIG. 5 are stored.

DESCRIPTION OF THE DRAWINGS

Figure 1:
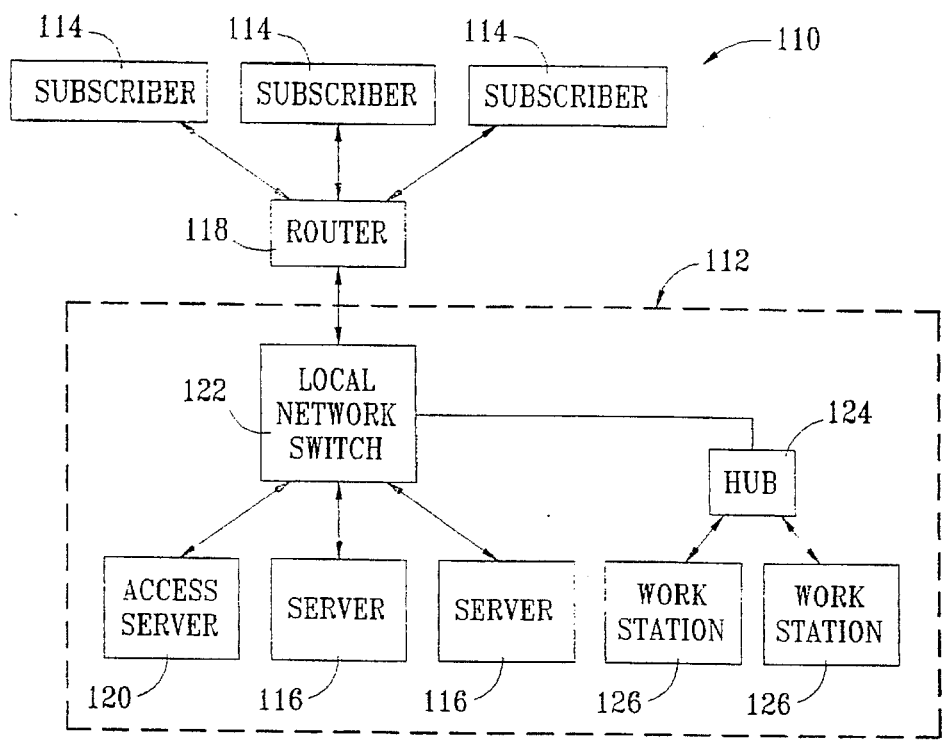
FIG. 1 is a schematic illustration of a computer network for maintaining and retrieving a document from a data repository for records and information concerning users subscribing to a network or affiliation of service providers.

Referring to FIG. 1 there is schematically illustrated a centralized, computer-based system 110 for receiving, storing and processing records for subsequent access by subscribing service providers such as physicians, clinics, hospitals, laboratories, insurance companies, researchers or other persons or entities requiring access to the records. The System 110 includes at least one network of server computers 112 organized as a local area network for serving a plurality of subscriber client systems 114 belonging to medical service providers. Client systems 114 can be stand-alone computers or networks of computers.

The network of computer servers 112 includes at least one, and preferably a plurality of server computers 116 that store medical record documents and data for each patient of each subscribing provider and execute processing applications programs relating to the documents. In addition to providing scalable processing capacity, use of a plurality of server computers 116 enables data back-up functions to be performed and provides redundancy to increase the reliability of the system. As is explained in connection with the description of the remaining figures, subscribing providers submit all medical records for their patients in either a hardcopy or softcopy form to a central complex of servers. Server computers 116 store patient medical records in the form received from providers as electronic files in a document file management system. The server computers 116 also store in databases data identifying the documents, data records containing basic or demographic information for each patient of each subscribing provider, and data relating to links between documents and patient records. In addition to running commercially available application programs such as database and file management programs which enable storing, maintaining and retrieving data and files, the server computers also execute several special application programs or processes. These applications include processes for automatically extracting data from documents, populate data bases with information extracted from documents and link documents to records of a patient based on data extracted from the documents.

In order to request and receive medical records and other patient information from server computers 116, the client systems 114 communicate with the network 112. Communications between the client systems and the server network are controlled with a router network 118 and a local access server 120. The local access server 120 provides network protocol translation and transaction routing and also hides details of server addressing within the network from the client or provider. Remote access to the server network 112 can also be provided through modem or ISDN line or as part of a wide area network. An additional server may be utilized to provide E-Mail services for delivering messages between providers.

Server computers 116 are interconnected using a switching network 122 for providing a packet and cell-switching back plane for the servers. Applications running on the server computers 116 utilize the TCP/IP protocol for local server network services and access to data and files stored within the network. Such a back plane supports multiple physical layer interfaces and provides a base for further growth in the capacity of the local network to service providers. The media for the local network is either switched Ethernet or FDDI. A plurality of local network workstations 126 used for server operations are segregated from the server backplane using switching hub 124 to increase the bandwidth of the backplane.

For larger installations, especially installations that span large geographic areas, the system is scaled, for example, by adding a plurality of local access sewers. Although not shown, each local access server is linked with one of a plurality of regional sever complexes, like server complex 112, each serving a different geographic region. Each regional server complex communicates with a master server. Generally, each regional server acts as host, storing copies of patient medical records received electronically from providers via the local access servers, and databases of information relating to the medical records and the patient. The master server stores master databases which reference the regional servers that host data for any particular patient or medical record. Each server in this system processes queries from a lower-level server or provider workstation. The servers also receive updates relating to database entries and data files.

When a server receives a request for a patient's records from either a subscribing provider or a lower-level server in the system, it sends a copy of all of the database entries that satisfy the query to the requesting computer, whether it is to another lower-level server or a subscriber. If a data file is requested, such as an actual medical record, only the requested data file is sent. If the local access server does not have database entries or data files requested by a subscriber, it will request the data files from a regional server and, when received, it will store the data files for transmission to the requesting subscriber. Since patient care usually takes place in localized episodes, copying database entries down to local servers tends to speed access times for other providers connected to the local servers. However, data files tend to be larger. Therefore, copying of data files down to local servers is limited to reduce disk space requirements for subscribing provider's workstations and local access sewers, since these computers will tend to be legacy equipment. Overall, by copying data down to more localized servers, system reliability is increased through computer redundancy.

The exact network configuration for a particular installation will depend on several factors, including the needs of the particular installation and the network systems available at that time. It may change with time due to changes in the number of providers and patients involved and with advances in networking techniques. One advantage of the illustrated network topology is that it can be scaled to the requirements of installation, from small to large, and grow as necessary to meet the demands of the system. However, other types of network media, topology and protocols may be substituted to meet the requirements of the particular installation.

Figure 2:
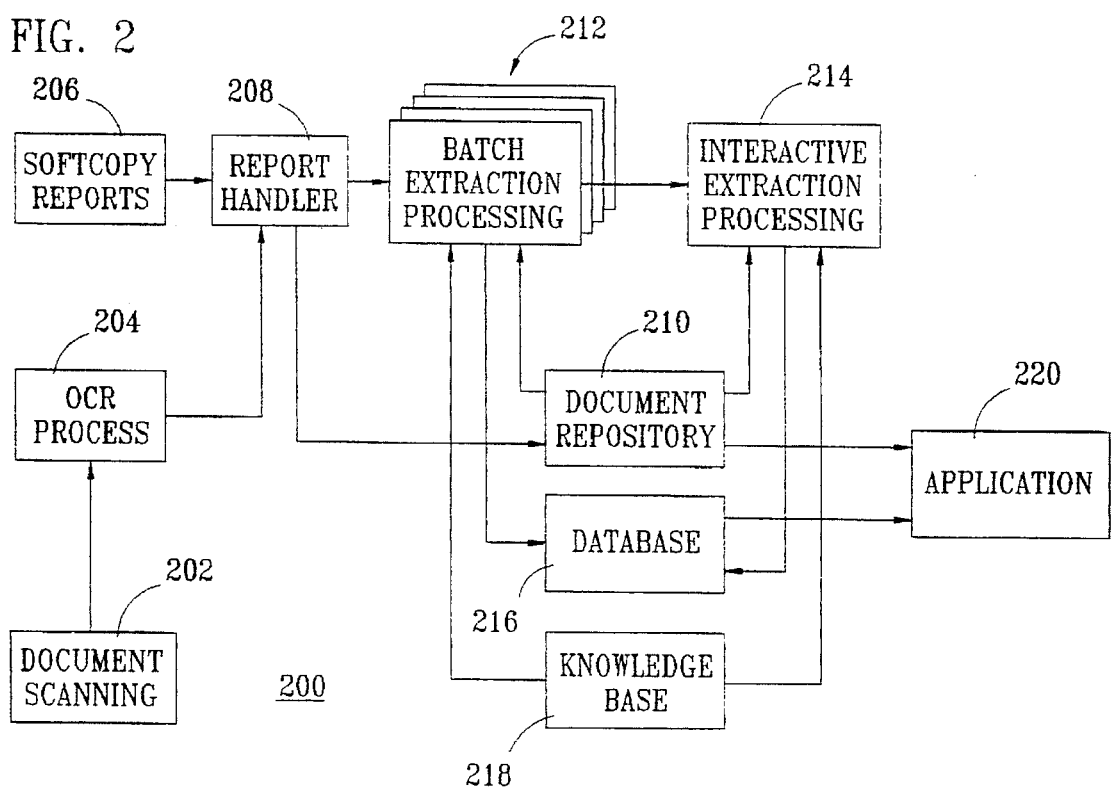
FIG. 2 is a functional block diagram of data processes for automated cataloging of documents received by the network of FIG. 1.
Figure 3:
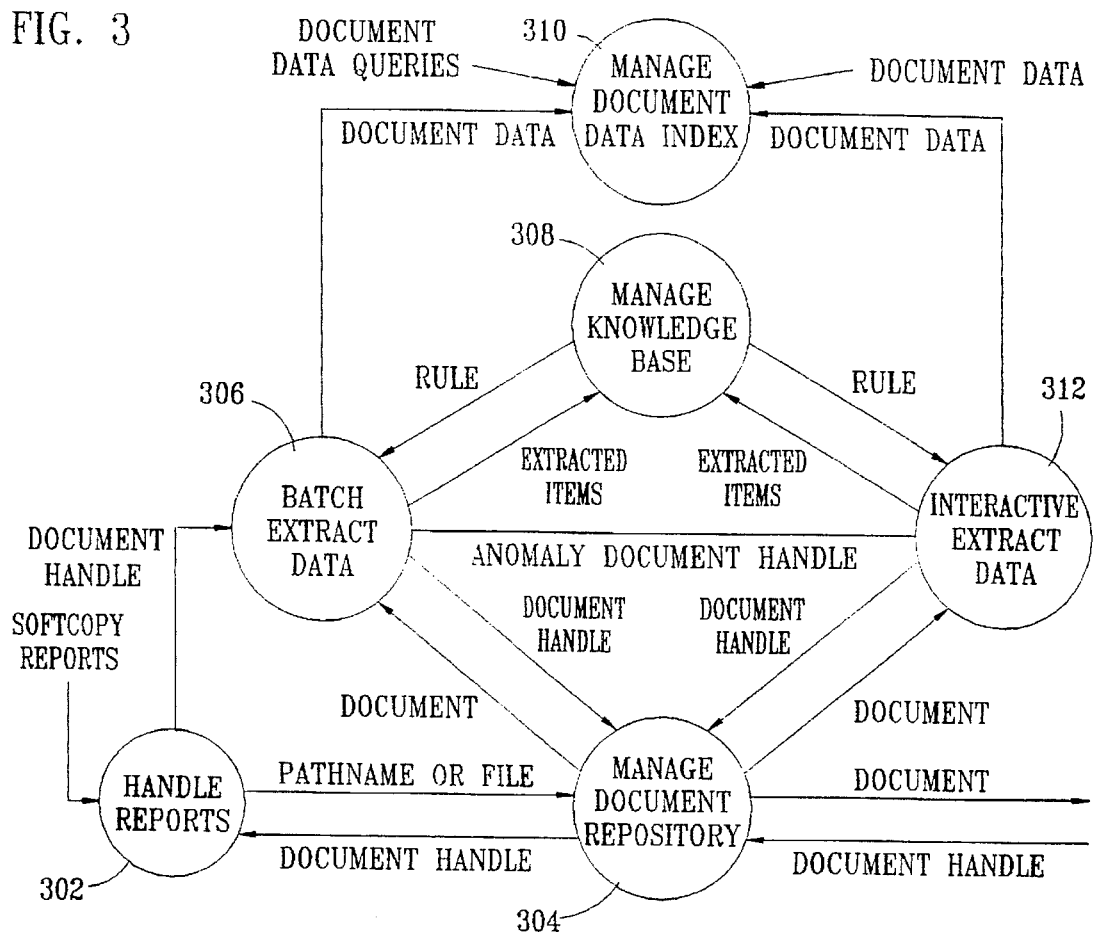
FIG. 3 is a schematic diagram illustrating the flow of data between functional processes of the system of FIG. 2.

Referring to FIG. 2 there is illustrated the basic interconnection between functional components of a data repository engine 200 for extracting from a document certain predefined data items including document identifiers and patient demographic information. FIG. 3 illustrates the basic process steps of the data repository engine 200 and the data flow between the basic process steps. Referring only to FIG. 2, the processing components of the data repository engine 200 include a report handler 208, document repository 210, batch data extraction program 212, an interactive extraction program 214 for anomalous documents, document identifier and patient demographic information database 216 and knowledge base 218. Briefly, the data repository engine receives a medical record report or document from a subscribing medical provider and extract values for pre-defined data items from the record. It catalogs the data and stores each medical record report or document as a data file in a repository for subsequent retrieval by subscribers or further processing. Various application programs 220 which are described in connection with other figures, make use of the extracted data. The processes of the data repository engine 200 are executed by the server computers 116 either sequentially or simultaneously, depending on demand for the process and available processing capacity of the servers.

The data repository engine 200 receives hardcopy or softcopy reports from medical service providers. Hardcopies of medical reports are sent by mail or transmitted by facsimile and are scanned by a document scanning process 202 to create a file containing the optical image of the document. Text in the optical image is then read by an optical character recognition process 204 to create a file, referred to herein as an "OCR file". The scanning and recognition processes can be performed off-site, using commercially available equipment and programs. The optical image file and the OCR file are then delivered on media or electronically transmitted to a server computer 116. Providers may also submit a softcopy report 206. The file is delivered on machine readable media, such as magnetic or optical tape or disk, or transmitted electronically to the server computer 116. The reports may contain fielded or structured data (e.g. database tables or formatted data files) or unfielded data (e.g. text in word processing files or ASCII files).

Referring to FIGS. 2 and 3, as generally indicated by handle report handler process 302, the report handler 208 receives each softcopy report, which also includes OCR files from OCR process 204, converts or normalizes it as necessary to an ASCII formatted text file or other standard format suitable for use by the processes of the document repository engine, and all versions of the documents are stored during the document repository 210. The report handle process 302 also provides the file or the pathname at which the file has been stored in memory to a document management program as generally indicated by 304 that is associated with the document repository 210. The document repository process may include, for example, a DOS file system for on-line storage and a tape file system for off-line archive storage. The document management program 304 assigns the report a unique document handle or identifier and provides the number to the report handler process 302. The report handle process 302 in turn distributes the unique identifier to the batch extraction process 306. The handle or other unique identifier uniquely identifies each medical record document stored in the system and enables other processes to request document files from the document management process without regard to their storage location.

The document management program 304 tracks files stored in the document repository 210, and retrieves document files in response to requests from other programs. These files are preserved in their original form to assure integrity of the data contained in the files. Copies of the files are only provided to processes when requested. Files containing an original document and other "views" of the text file, for example scanned images of hardcopy reports, are stored and associated by the document management program with the text file of the document. Commercially available programs may be used for file and document management.

The batch extraction program 212 includes a rules-based application program which automatically extracts certain specified document identifying data from text files. The execution of the rules by the application program is generally represented by batch extract data process 306. In batch extraction process 306, a document handle is received from the report handler process 302 for a newly received document. With the document handle, the batch extraction process requests from the document management program 304 a copy of the text. The extraction process obtains rules from knowledge base 218 that guides extraction of values specified data items from the file. A rule is a list of methods that, when executed, results in obtaining a value or data string for particular data items. The data extraction process 306 receives a rule from the manage knowledge base process 308, executes the rule and returns the extracted value to the manage knowledge base program 308. If the data item that is returned is of an acceptable value, the data value is communicated to a database management process 310, performed by a database management system (DBMS) application program, which stores the extracted document data in database tables that are set up in document identifier database 216 and pointers to the original documents. The database management process 310 responds to queries for document identifying data from other applications running on the server computer 116, which are collectively represented by the application block 220.

Neither the documents ingested by the data repository engine nor the data they contain need conform to predefined formats for data extraction to take place using a variety of methods. The document may contain structured data, unstructured data, or both. Structured data includes, for example, fielded data, such as database tables, and other types of formatted data files. Examples of medical records which include structured data are lab database tables, research database tables and other types of data files which are formatted according to predefined formats such as HL7. Structuring of the data enables ready identification of the fields or data elements containing data values to be extracted. Examples of unstructured data or, in other words, information which contains no data structure, includes free form text in ASCII format or word processing formats, graphs, and compound documents. Examples of documents with unstructured data include result reports status reports, and patient registration forms. The extraction rules for each type of document are stored in the knowledge base 218 and include, various methods for extracting data from unstructured or structured data sources, or both, depending on the type of document and the specific data to be extracted. The specific rules are developed from knowledge concerning the document that is provided by subscribers or that is gleaned from medical records actually submitted by medical providers.

If the batch extraction process 212 encounters a document for which it cannot extract the necessary information, the document handle is forwarded to the interactive extraction process 214 as an anomalous document. As indicated at 312, the interactive extraction process 214 involves retrieving the ASCII text file from the document repository process 210 by presenting the document handle to the document management process 304. A human interpreter views the document and interacts with the manage knowledge base process 308. Rules are provided from the knowledge base 218 to the interactive extraction process 312. The human interpreter manually resolves and augments any unresolved extraction operation. If the document is a new type of document, additional extraction rules can be added to the knowledge base 218 for future processing.

Figure 4:
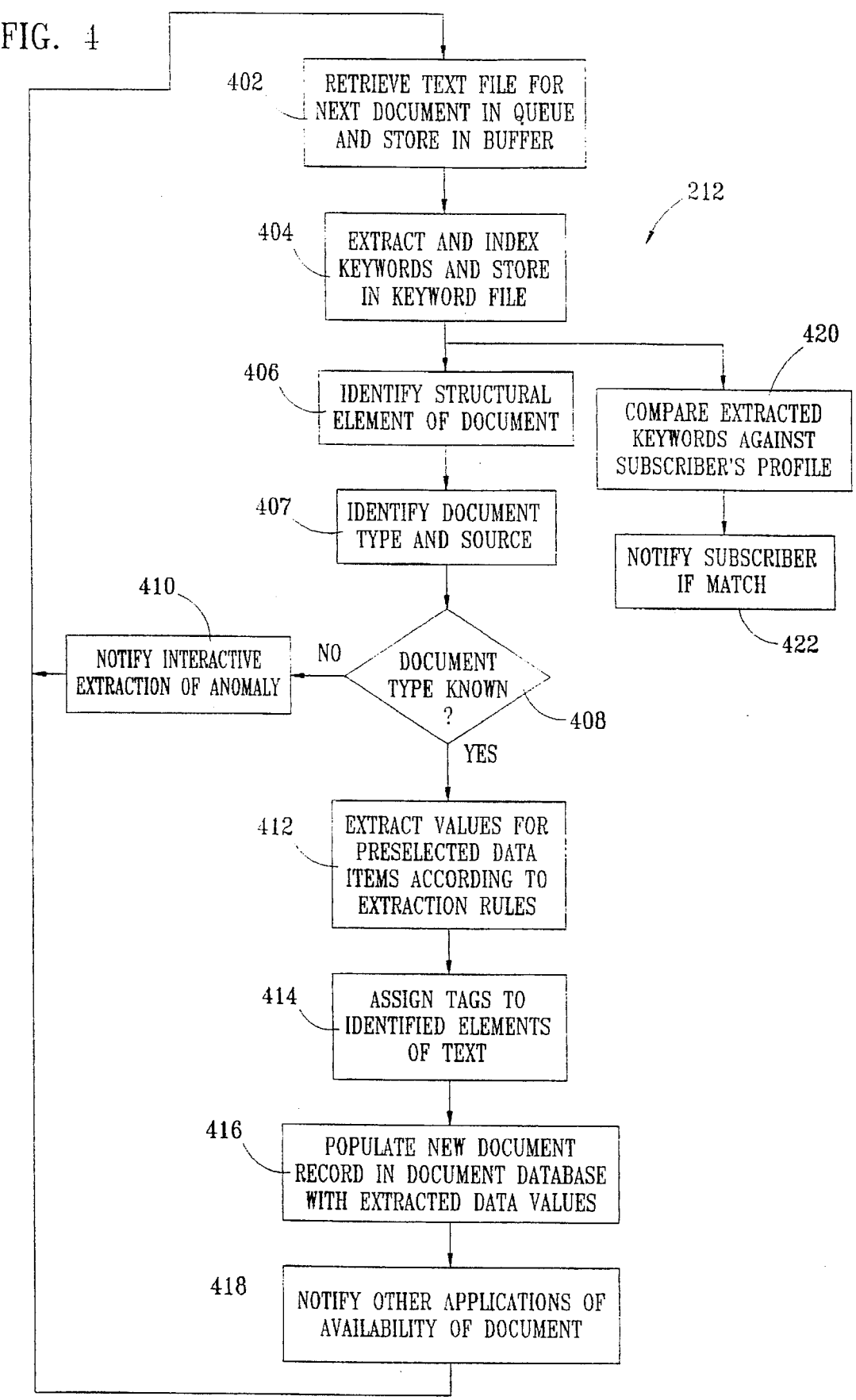
FIG. 4 is a flow diagram of a batch extraction process that is part of the automated cataloging process of FIG. 2.

Referring to FIG. 4, there is illustrated a flow diagram showing steps of the batch extraction process 306 for an unstructured text file. Unstructured text has no predefined data fields with predefined formats. The knowledge base 218 includes rules for execution by the batch extraction process 306 for extracting structured data and unstructured codified data. Extraction of structured, codified data involve techniques well-known in the art. Thus, will not be detailed here. However, the batch extraction process 306 executes additional steps which facilitate extraction of data items from unstructured or unfielded text.

In order to automatically extract data from an unstructured text file, the data elements for which values are desired must first be located within the unstructured text. Only then can values for the data elements be extracted and stored or passed in a corresponding data field of the database 216. In the illustrated process, values for the data items to be extracted are stored in the database 216.

Document files waiting for data extraction are queued for the extraction process, using document handles, by the report handler process 208. As indicated by step 402, the process begins by retrieving the next unstructured document in queue from the document repository in the manner described in connection with FIG. 3, and storing it in a text buffer. The text buffer forms part of a "document object" created for each document during the data extraction process. At step 404, the process removes stop words such as "a" and "the" from the text. The remaining keywords are then indexed and stored as a keyword file that is associated with the text file. The keyword file is utilized in later steps of the extraction process, as well as in a notification process indicated by steps 420 and 422. The notification process will be discussed after the extraction process.

To assist in the process of extracting data, the basic structural elements into which the unstructured data is spatially organized in a document are first identified in step 406 using a set of rules stored in knowledge base 218 (FIG. 2). The structural elements of a document may include, for example, a header, a footer, a body consisting of one more sections, a title and a subject.

Figure 5:
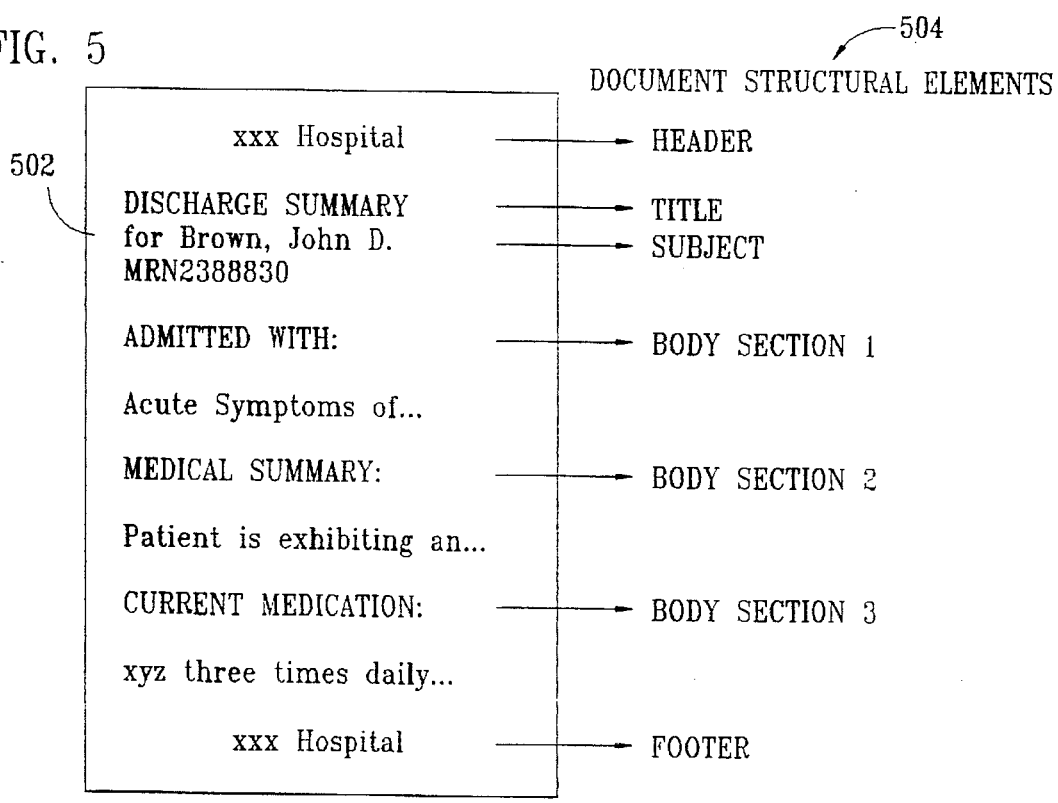
FIG. 5 illustrates a representative document containing unformatted text and identifies structural elements of the document.

Referring to FIG. 5, there is illustrated an example of a medical document 502. The identities of its structural elements as listed in column 504. The structural elements are used to guide or further aid in the document identification and data extraction process by extraction rules stored in knowledge base 218. These extraction rules rely also on well-known techniques to identify a data element such as positional (e.g. row, column, delimiter) and keyword positional (e.g. remainder of line following a keyword), and combinations of these techniques.

The extraction process attempts, at step 407, to automatically identify the document's type. For example, is the document an admission form from hospital "x," operative notes from hospital "y" or a blood test from lab "c"? To find the name of the source of the document, the document's header and footer are searched for character strings containing the name of a subscribing organization or an alias (e.g., abbreviation) of the name. The type of document can be determined by searching the title for certain character strings that indicate the document type. Generic titles such as "Blood Test" or "Discharge Summary" reliably indicate document type. In other cases, additional rules may be required which depend on prior knowledge of specific document type. For example, a certain originator of a document may use a different title for a document of the same standard type. Instead of "Operative Notes" it may use "Surgery Notes." These character strings are searched for in the title of the document. If, as indicated by decision step 408, the document type cannot be identified, or document identifiers cannot be extracted, the interactive extraction process 214 (FIG. 2) is notified at step 410 that the document is anomalous.

At step 412, once the document's type and source are identified, values for additional document identifying information and for patient demographic information, including a medical record number, are extracted. For example, a medical record number assigned by the document's source will typically be next to (e.g. above, below or following) the character strings "MRN" or "Medical Record." The exact string and location will depend on the source of the document and its type. The name of the attending or responsible clinician can be extracted from the document using a rule from the knowledge base 218 that directs searching for a string such as "Attending Physician:" and extracting from the text the immediately following character string. The name of the patient may follow the string "Patient Name:" or may be, in certain documents, on the third line. A priori knowledge, gleaned from previously submitted documents of the same type and origin, of the location or context of the data item within the text of the particular document may also be required, however, to extract the value for the data item. For example, once the type and origin of a document is known, a rule based on prior knowledge concerning a document of that type from that source may instruct the process to go to line 3 of the text and look for the string "Attending Physician" to extract the following character string. The name of the patient may follow the string "Patient Name:" or may be, in certain documents, on the third line. Values which are extracted are then assigned to a data item in an object file created for the document.

At step 414, the process creates tags for some or all of the structural elements of the document. Each tag includes a generic term for the section (e.g., "Body Section 3") followed by a medically-relevant term such as "Current Medications." The medically relevant term is assigned based on the identification of the document's type or other information extracted from that section of the document using rules stored in knowledge base 218 (FIG. 2). The tags and the lines at which each section starts and stops are stored in a separate file that accompanies or is associated with the document file. File 900 of FIG. 9 is an example of such a portion of such a tag file. A delimiter character, such as a period, separates the two terms and indicates the beginning and end of the tag within the tag file. Relevant or important sections of the document can then, if desired, be linked to a master patient identifier for the patient. Sections of the document, rather than the entire document, can thus be searched for and retrieved, thereby reducing time required for locating pertinent information, especially if many medical records are retrieved for review. For example, only current medication sections from stored medical documents can be retrieved for review.

At step 416, a new record is created for the document in database 216 and the fields of the record populated with the corresponding values that were extracted from the document. The record is associated with the text of the document and other versions of the document that are stored in the document repository process 210 using the document's unique identifier or handle. Patient demographic information is also extracted from the document at this time and stored for use by a master patient index (MPI) Populator application process described in connection with FIG. 6. After extraction is completed, other applications or subscribers are then notified at step 418 of the availability of the document for further processing or review, such as by the MPI populator process illustrated in FIG. 6. The batch extraction process returns to step 402 and begins again with the next document in the queue.

In a separate application process, indicated by steps 420 and 422, the keyword file for each document is compared to profiles set up for each subscriber. If there is a match between keywords of a document and a profile, the subscriber is notified of the availability of the document. The subscriber profile may include, for example, a list of names of patients of the subscriber and other keywords that indicate the document is relevant to the subscriber's care for the patient. For example, a keyword could be the names of certain diagnostic tests. The subscriber is then notified of tests for a given patient that have been performed by other providers to avoid repeating the tests. Another example of key words would be names of hospitals or other words that are typically found on hospital admission forms. The subscriber is then informed that one of its patients has been admitted to a hospital.

The steps of the interactive extraction process 214 (FIG. 2) are not illustrated but proceed in a method similar to that of the batch extraction process. The interactive extraction process 214 preferably draws upon knowledge base 218 for rules and other information to interactively guide an operator, to the extent possible, through the same steps as the batch extraction process of FIG. 4. The interactive extraction processing may be completely manual or semi-automatic, by automatically extracting certain data values, while pausing and prompting the operator to resolve or validate application of other rules that it cannot otherwise execute. For example, rules on categorizing or typing of the document may prompt for the operator to select a proper document type. Rules containing aliases, such as abbreviations, for sources assist the operator in resolving and entering the correct source of the document. Preferably, the knowledge base 218 is updated with information concerning the particular document being processed to enable batch processing of the same type of document the next time one is received.

Figure 6:
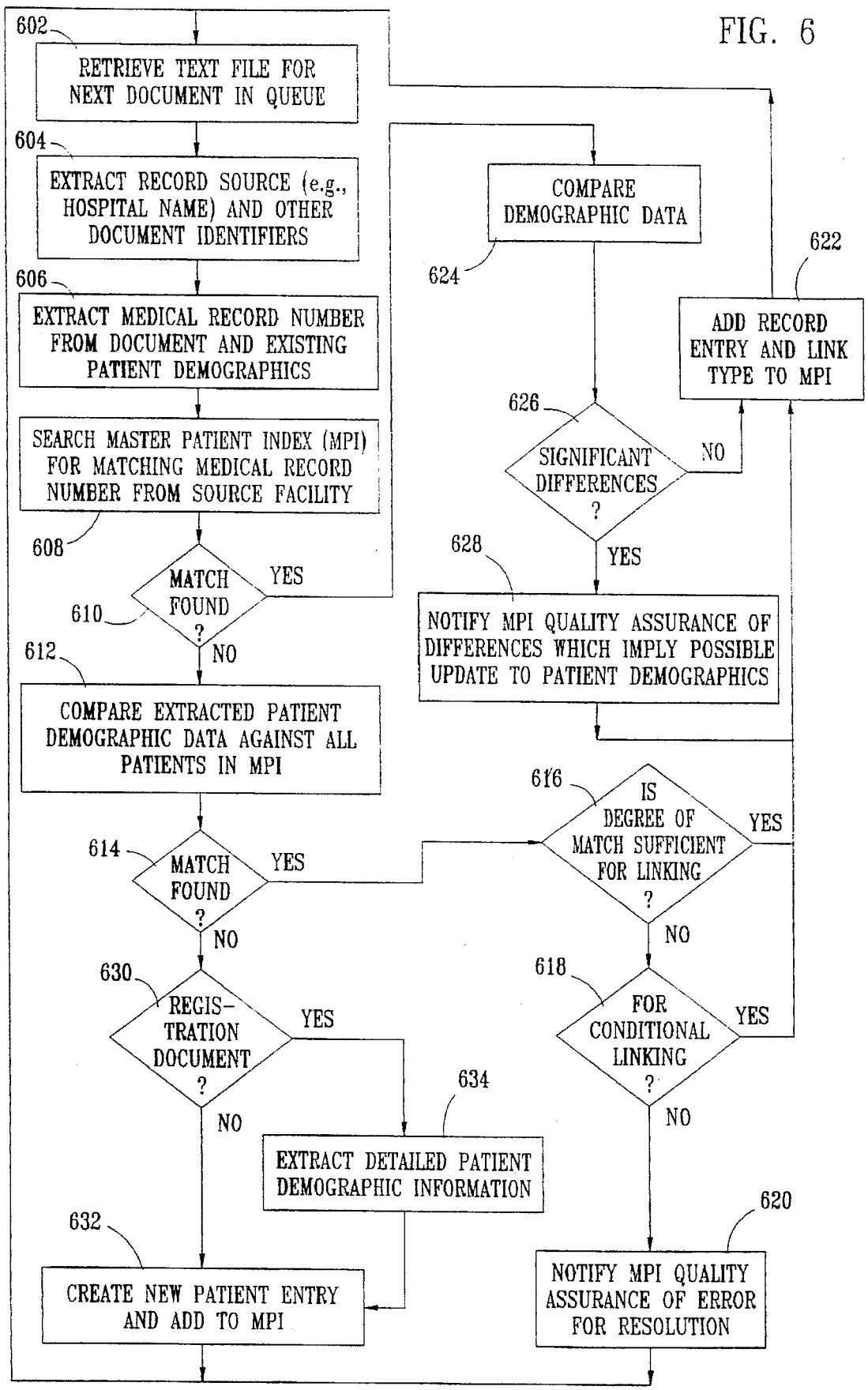
FIGS. 6 is a flow diagram of a process for linking a medical document to a patient master record using information extracted from the document.

Referring to FIG. 6, a master patient index (MPI) populator and linking process running on the server network 112 (FIG. 1) performs two basic functions. First, it automatically populates database 216 (FIG. 2) with patient demographic information extracted from medical records submitted by subscribing providers. Patient demographic information stored in database 216 is referred to as the MPI database. The MPI database includes structured data files which contain information on all patients who have been treated by, or otherwise receive the services of, a subscribing provider. The system assigns to each patient a unique master patient identifier. The MPI Populator attempts to maintain only one identifier for each patient. Associated with the identifier in the MPI database is patient demographic data, including current name, sex, date of birth, and social security number of the patient. The MPI database also includes a listing of all medical record numbers assigned to the patient by subscribing providers.

Second, the MPI Populator process automatically links medical documents received and processed by the data repository engine 200 of FIG. 2 by matching patient demographic data contained in the MPI database to the data extracted from the documents. A listing of all links between documents stored in document repository and the patient identifier made by the MPI Populator is maintained in the MPI database.

Steps 602, 604 and 606 are performed by the batch extraction process 306 or the interactive extraction process 312 in the manner previously discussed in connection with FIGS. 3 and 4. At step 602, the text file of the next document in a queue is retrieved. At step 604, the source of the record or document and other document identifiers are extracted. As indicated by step 606, any medical record number contained within the document and any basic patient demographic information in the document is extracted. Both document identifiers and patient demographic information can be extracted as part of the same or different batch extraction process and/or interactive extraction process.

Beginning at step 608, the MPI Populator process attempts to link the document to a specific patient. First, it searches for a matching medical record number in the lists of medical record numbers by facility or source maintained for each patient in the MPI database. A unique match must be found, meaning that no other patient identifier has the same medical record number from that facility or source. If, at decision step 610, there is no unique match, the process then begins comparing other extracted patient demographic information to that stored in the MPI database. At step 612, the MPI populator process begins the matching process for the demographic information. For purposes of facilitating the matching process, the data items that are matched may be limited to patient name, aliases (e.g. maiden name), social security number, sex and date of birth, which information is maintained in a separate table in the MPI database. The Populator process searches the MPI database for matching demographic information. If, as indicated by decision step 614, a match is found, the MPI Populator process determines, as indicated by decision step 616, whether the degree of matching is sufficient for linking. A high degree of confidence in the match to the patient identifier is required to unconditionally link the document to a patient. If there is some degree of matching, though not of a type to create a high degree of confidence (e.g., a name only), a conditional or fuzzy link may be made as indicated by decision step 618. Generally, an exact match between the extracted value of the extracted data item and the data stored in the corresponding field of the MPI database is not always possible or expected. For each field there is maintained a definition of what constitutes a match for that field. For example, a patient name extracted from the document will be compared against the patient name stored in the MPI database and patient aliases stored in the MPI database, for names with the same or similar spellings or that sound similar. Exact matches are given stronger weight than close matches. The weight of individual field matches for any one particular patient record is then totaled to determine the strength of the match. The weight given to the match in each field and the total strength of the match to a patient can also be varied. A fuzzy link will be made only to the patient record having the strongest match if that match exceeds the threshold for making a conditional match. A fuzzy link can then be reviewed later to either break the link or to remove the condition when additional or updated information on the patient or document is obtained. If no link is made, a quality assurance process is notified of the error and provided with suggested patient records for further resolution as indicated by step 620. The quality assurance process notifies a database integrity specialist. The quality assurance process provides a user interface and extraction, query and association capabilities required for the specialist to resolve the anomaly. If a match has been made, the process continues at step 622 by adding the document's unique identifier, the patient identifier, and the type of link made to a linking table stored in the MPI database.

If a match was made by MRN at step 610, the demographic information that has been extracted and stored in a document is compared to the most current demographic information stored in the database for the patient at step 624. If there are any significant differences, as indicated by decision step 626, they are reported at step 628 for review by a person functioning in a quality assurance capacity who may then update the patient's current demographics. The process then adds the new records at step 622 and returns to step 602.

If no match is made at steps 610 or 614, the process assumes that the patient is new. If the document is a registration document, as indicated by decision step 630, the process creates a new patient record in the MPI database and populates the record with additional, detailed demographic data extracted which a registration document is likely to contain, as indicated by steps 632 and 634, using the batch extraction process 306 or, if necessary, the interactive extraction process 312 (FIG. 3). Registration documents include, for example, hospital admittance forms, new patient information forms or other documents that a patient may fill out upon retaining the services of one of the subscribing providers. Otherwise, a new patient entry or record is created and added to the MPI database at step 632 and populated with demographic information, if any, extracted at step 606. The MRN and source extracted at steps 604 and 606 are added to database 216 (FIG. 2) and linked to the patient record in the MPI database. The unique document identifier is then linked with the new patient identifier as the first entry in the MPI. The process then returns to step 602.

Figure 7:
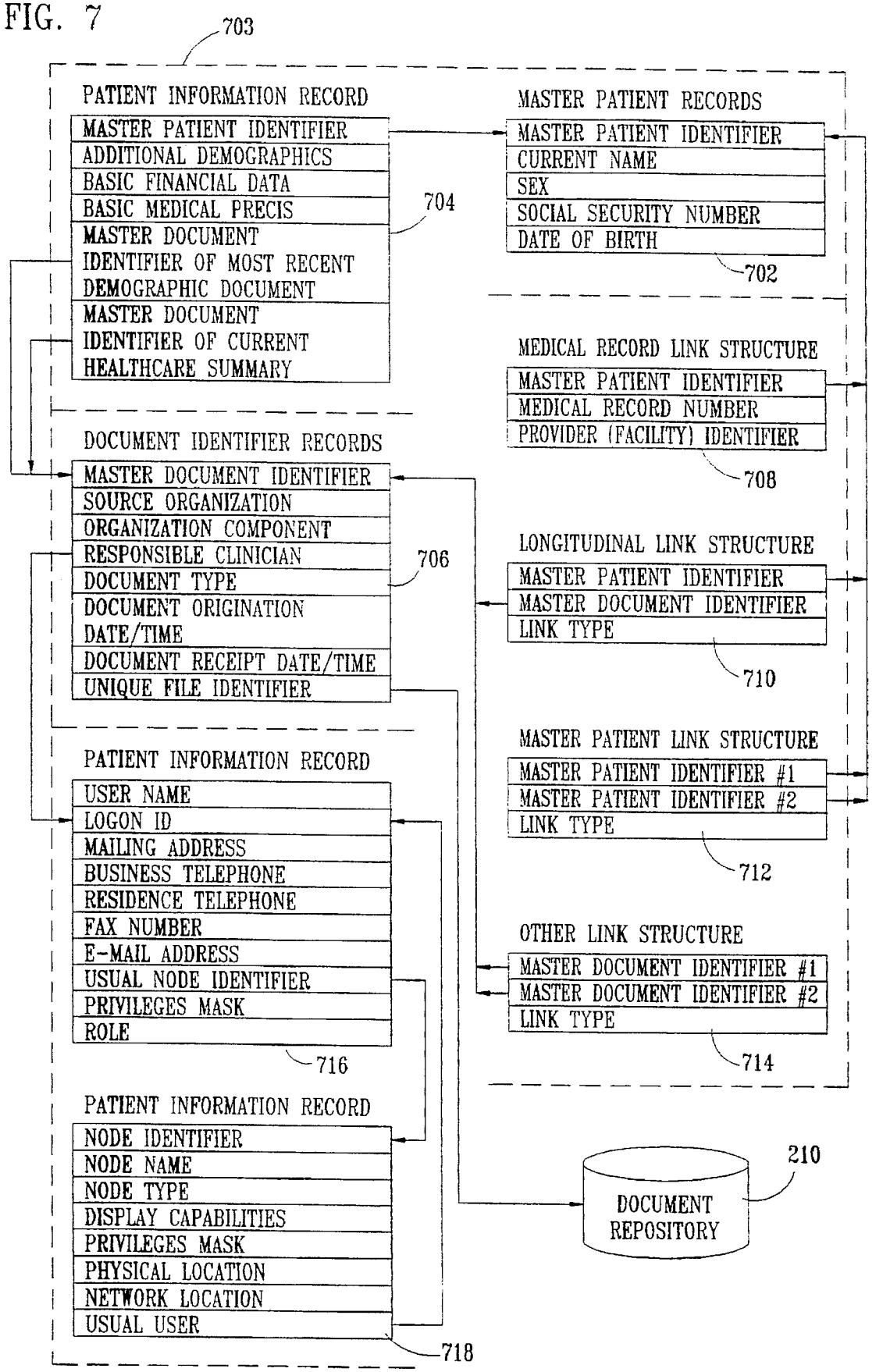
FIG. 7 illustrates the structure of tables in databases for storing information relating to patients, documents, and the links between patients and documents for facilitating retrieval by medical service providers of information and documents concerning a patient.

Referring now to FIG. 7, there is illustrated the structure of tables of data stored by the server network 112 (FIG. 1) in the database 216 (FIG. 2). These database tables enable inquiry and retrieval by subscribers to the system of basic patient and document information, as well as retrieval of documents linked to the patients.

For each master patient identifier there is one record in table 702. The fields in the record include the master patient identifier and basic demographic data that is the primary data used by MPI Populator process for matching a patient to a document. Table 704 contains a record for each master patient identifier. The fields store more detailed demographic information on the patient. Furthermore, it includes fields for basic financial data, medical prescriptions, and master document identifiers for the most recent records containing demographic data and a health care summary of the patient. The MPI Populator process fills in tables 702 and 704 with the demographic information extracted during running of the Populator process. Records in tables 702 and 704 are associated with each other by the master patient identifier and comprise the MPI database, as indicated by dashed line 703.

Table 706 comprises part of document identifier database 216 and contains, for each document, a record that includes fields for a master document identifier, receipt date/time and a unique file identifier. Data values for these fields are assigned to the document by the server network 112. Fields for the organization and components thereof that originated the document, the responsible clinician, the document type and the document origination date/time are also included and correspond to data items populated with data values extracted from the document by the extraction processes 212 and 214.

Medical record link table 708 lists links between each patient, as identified by a master patient identifier, and each medical record number that has been assigned by a subscribing provider to the patient. The master patient identifier associates each record in the table to a record in master patient record table 702. The medical record link table 708 thus serves as a list of all medical record numbers assigned to a particular patient that facilitates the linking of a document to a patient using a medical record number as described in connection with MPI Populator process of FIG. 6. A record is created for each new medical record number which is extracted from a document that has otherwise been matched to the patient or which has been otherwise associated to the patient. The provider or subscriber which assigned the medical record number is also listed in a separate field in the link record.

Table 710 stores longitudinal links between a patient and a document thereby providing a list of documents associated with each patient. Each record in the Table 710 contains a master patient identifier, a master document identifier and a link type. Each record in the table 710 is associated with the master patient record in the table 702 by the master patient identifier and also associated in the document identifier table 706 with the master document identifier.

Table 712 contains records which link two master patient identifiers in the event that it is later determined that the same patient has been assigned two master patient identifiers. Each record contains fields for each master patient identifier and a link type. For example, if it has been determined that two identifiers refer to the same patient, a "same patient" type of link is established. If it is resolved that two master patient identifiers refer to different patients, but with enough similarities to indicate a potential match, a "different patient" link type is indicated. A record in the table 712 is associated with a record a master patient record in the table 702 using master patient identifiers.

Table 714 contains information to enable related documents to be linked. For example, medical records relating to the same episode of care are linked to facilitate subsequent retrieval and review. The type of link and the master document identifiers are stored in different fields of the record.

Another database stores information relating to access and use of the system by subscribers. In table 716, each authorized subscriber has a record which includes the subscriber's name, log on identification, and other basic information such as address, role (such as "primary care physician") and telephone numbers. Additionally, each record contains a field for an E-mail address and the identifier of the user's usual node in order for the system or another subscriber to communicate with the subscriber. The record also contains a privileges mask and the user's role for use in supporting system security. Information on each subscriber node such as client system 114 within the computer-based system 110 is stored in a separate record in table 718. This information includes an unique node identifier assigned by the network which associates the node with a user in user information table 716, node name and type, and the nodes physical location and network location. Additionally, the display capabilities of the subscriber's equipment of the node is indicated so that documents are sent in a version and format that can be displayed. Additionally, the record keeps track of the privilege level of the node and the log on identification of the usual user of the node for security purposes.

Figure 8:
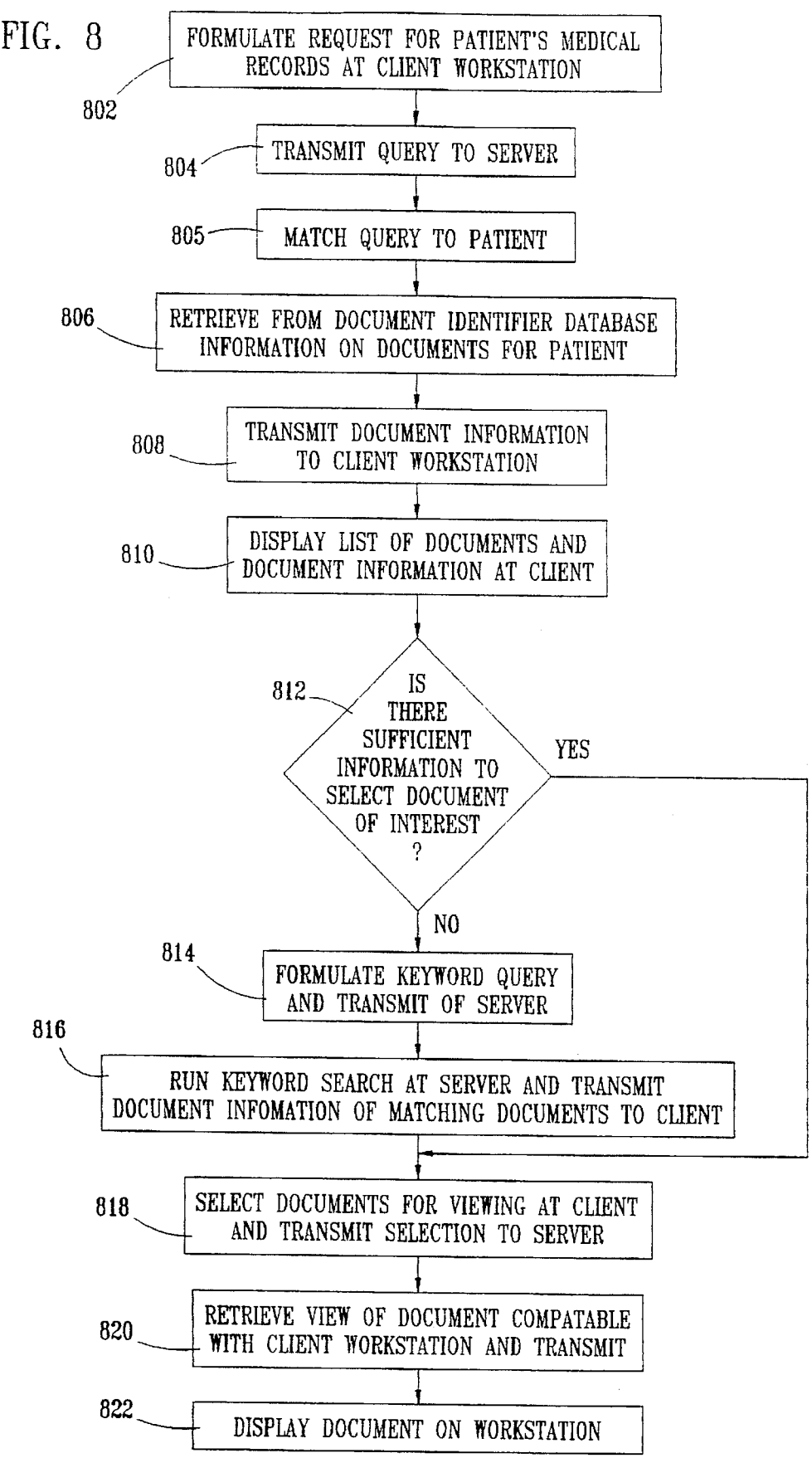
FIG. 8 is a flow diagram of a representative process of retrieving a document and other information concerning a patient from a central document repository.

Referring now to FIG. 8 each client workstation 114 runs an application program for enabling a subscriber to formulate queries to be sent to the server computers 116 of server network 112 for discovery and to retrieve medical documents stored in the document repository 210, and that displays the information and documents retrieved from the servers. The database management application program running on the server computer 116 process the queries and transmits information concerning documents matching the queries and selected documents to the client workstations. The process of FIG. 8 illustrates steps of a typical process of a subscriber obtaining a medical document.

Beginning at step 802, a subscriber formulates a request at one of the client systems 114 for a patient's records using the medical record number assigned by the subscriber to the patient. If it is a new patient for the subscriber, the subscriber may identity the patient by name and other demographic information such as sex, date of birth and social security number. The application running on the work station interprets the request and formulates a query and transmits it, at step 804, to the server network 112.

At step 805, the query is presented to the master patient index database for matching to a patient record using master patient records table 702 (FIG. 7). If a patient match is found, identifying information on the documents linked to the patient in longitudinal link table 710 is retrieved from the document identifier database 216 (FIG. 2). This information is then, at step 808, formatted and transmitted to the client system 114.

At step 810, the client system 114 displays a listing of the documents for review by the subscriber. The listing includes information such as document type, data, source of the document. The information that is displayed is intended to enable a subscriber to select documents of interest for further viewing. Depending on the application, more or less information can be displayed. The document information may, in some cases, be insufficient to enable a subscriber to determine which documents are of interest. If the subscriber is unable to determine which document or documents are of interest, as indicated by decision step 812, the subscriber formulates a keyword query at step 814 and transmits it to the server network 112. At step 816, the server network 112 performs the keyword query by searching for the keywords in the text of the listed documents. A listing of documents satisfying keyword query is transmitted to the client system 114 for display.

At step 818 the subscriber selects one of more documents for viewing and transmits a request for the documents to the server network 112. The server network 112 at step 820 retrieves each document requested from the document repository 210 (FIG. 2) and transmits it to the client system 114 in a version (e.g. text or image) and a format compatible with that system's display capabilities. The system's display capability is indicated in table 718 (FIG. 7). The client system 114 then stores and displays the document at the client system at step 822 when received. If the client system does not have the capability of displaying the document, the document is printed off-line and sent by mail or is transmitted by facsimile.

Other information, other than simply a listing of documents concerning the patient, can be obtained from the patient information table 704 using similar query processes. For example, the most recent document summarizing the health care of the patient is quickly available using the master document identifier listed in the patient information table. For research purposes, more complex queries may be formulated that combine keyword searching of documents with fielded queries for matching to patient demographic information and document information stored in the structured databases. Additionally, a subscriber may specify by sending from the client system appropriate commands to the server network to limit search to documents having a certain tag associated with it. Tags are described in connection with FIGS. 4 and 5. Before sending the documents, the server network can review the tag file associated with the patient's documents to determine whether the document is relevant, and then extract from the document file and transmit only the tagged section or portion for review.

The foregoing description is of a preferred embodiment of the invention. Since variations of this embodiment may be made by those persons skilled in the art, the inventions should not be construed as being limited to the form set forth, but to encompass other forms as may fall into the scope of the appended claims.

What is claimed is:

1. A method of extracting a pre-defined data item from unstructured medical service records stored in a central data processing system and generated by a plurality of service providers, comprising the steps of:

storing the unstructured medical service records in a database of the central data processing system for a plurality of individuals having previously sought or received services from at least one of a plurality of service providers, each unstructured medical service record contains a plurality of spatially-organized groupings of unfielded and free form text;

identifying each spatially-organized grouping as one of a plurality of structural element designations using a rules-based application predicated at least in part on the structural element designations and a document type associated with a particular service provider; and extracting the pre-defined data item from one of the plurality of spatially-organized groupings by executing the rules-based application.

2. The method of claim 1 wherein the step of identifying the spatially-organized groupings further includes identifying one of the plurality of generic structural element designations from the group header, title, subject, footer and a plurality of body sections.

3. The method of claim 1 wherein the step of extracting the pre-defined data item includes identifying medically relevant data, demographic information and a medical record number associated with the individual.

4. The method of claim 1 wherein the step of extracting the pre-defined data item further includes developing rules utilized by the rule-based application from information provided by the service providers or a previous unstructured medical service record.

5. The method of claim 1 further comprising the step of forming a TAG file including:

developing generic terms indicative of the structural element designations;

inserting the extracted pre-defined data items adjacent to the generic terms associated therewith; and linking the TAG file to the medical service record.

6. The method of claim 5 wherein the step of extracting the pre-defined data item further includes:

obtaining rules from the rules-based application for extraction of the pre-defined data item from the unstructured medical service record;

executing the rules to obtain the pre-defined data item;

storing the acceptable pre-defined data item in the TAG file; and linking the TAG file to the medical service record.

7. The method of claim 1 wherein the step of identifying each spatially-organized grouping includes the steps of:

removing stop words from the medical service record such that keywords remain in the medical service record;

storing the keywords in a keyword file; and associating the keyword file to the medical service record.

8. The method of claim 1 wherein the step of identifying each of the spatially-organized groupings includes identifying the document type by utilizing the structural element designations.

9. The method of claim 1 further comprising:

creating a new medical service record associated with the medical service record in the database, said new medical service record includes a plurality of data fields;

populating the data fields of the new medical service record with the extracted pre-defined data; and storing the new medical service record in a document repository using a document handle.

10. A method of extracting medically related information and demographic information from unstructured medical service records stored in a central data processing system and generated by a plurality of service providers, comprising the steps of:

storing the unstructured medical service records in a database of the central data processing system for a plurality of individuals having previously sought or received services from at least one of a plurality of service providers, each unstructured medical service record contains a plurality of spatially-organized groupings of unfielded and free form text;

identifying each spatially-organized grouping as one of a plurality of structural element designations using a rules-based application predicated at least in part on the structural element designations and a document type associated with a particular service provider;

developing rules utilized by the rule-based application from information provided by the service providers or a previous unstructured medical service record;

extracting the medically relevant information and demographic information from one of the plurality of spatially-organized groupings by executing the rules-based application;

creating a new medical service record associated with the medical service record in the database, said new medical service record includes a plurality of data fields;

populating the data fields of the new medical service record with the extracted pre-defined data; and storing the new medical service record in a document repository using a document handle.

11. A method of extracting pre-defined data items from unstructured medical service records stored in a central data processing system and generated by a plurality of service providers, comprising the steps of:

storing the unstructured medical service records in a database of the central data processing system for a plurality of individuals having previously sought or received services from at least one of a plurality of service providers, each unstructured medical service record contains a plurality of spatially-organized groupings including a header, title, subject, footer and a plurality of body sections;

identifying each spatially-organized grouping as one of a plurality of structural element designations using a rules-based application predicated at least in part on the structural element designations and a document type associated with a particular service provider;

developing rules utilized by the rule-based application from information provided by the service providers or a previous unstructured medical service record; and extracting the pre-defined data item from one of the plurality of spatially-organized groupings by executing the rules-based application.

* * * * *